United States Patent [19]
Hanson et al.

[11] Patent Number: 6,118,048
[45] Date of Patent: Sep. 12, 2000

[54] TRANS-DOMINANT INHIBITION OF GEMINIVIRAL DNA REPLICATION BY GEMINIVIRUS REP GENE MUTANTS

[75] Inventors: Stephen F. Hanson, Madison; Douglas P. Maxwell, Verona, both of Wis.

[73] Assignee: Wisconsin Alumini Research Foundation, Madison, Wis.

[21] Appl. No.: 09/065,999

[22] Filed: Apr. 24, 1998

Related U.S. Application Data

[60] Provisional application No. 60/044,925, Apr. 25, 1997.

[51] Int. Cl.[7] ............................ C12N 5/04; C12N 15/33; C12N 15/82; A01H 5/00; A01H 5/10
[52] U.S. Cl. ..................... 800/280; 435/69.1; 435/320.1; 435/419; 435/468; 536/23.72; 800/301; 800/313
[58] Field of Search .................................. 435/69.1, 410, 435/419, 468, 320.1; 536/23.72; 800/278, 279, 280, 295, 298, 301, 313

[56] References Cited

FOREIGN PATENT DOCUMENTS

WO 97/39110   10/1997   WIPO .................. C12N 5/14

OTHER PUBLICATIONS

Nejidat et al, Physiol. Plant., vol. 80, pp. 662–668, 1990.
Sijen et al, MPMI, vol. 8, pp. 340–347, 1995.
Koonin et al, J. Gen. Virol., vol. 73, pp. 2763–2766, 1992.
Russell et al, Plant Cell Rep., vol. 12, pp. 165–169, 1993.
Anderson et al, Proc. Natl. Acad. Sci., USA, vol. 89, pp. 8759–8763, 1992.
Hanson et al. "trans–Dominant Inhibition of Geminiviral DNA Replication by Bean Golden Mosaic Geminivirus rep Gene Mutants," *Phytopathology* 89:480–486.

*Primary Examiner*—Elizabeth F. McElwain
*Assistant Examiner*—Ashwin D. Mehta
*Attorney, Agent, or Firm*—Quarles & Brady LLP

[57] ABSTRACT

A genetic construct comprising a trans-dominant inhibitor of geminiviral replication is disclosed. When expressed in a plant cell, this inhibitor is able to dramatically reduce replication of geminivirus. Genetic constructs that include sequences containing portion of the ac3 gene in addition to the trans-dominant inhibitor exhibit increased efficiency and broadened specificity of inhibition of geminiviral replication. A method of protecting plants against geminiviral infections is also disclosed.

16 Claims, 1 Drawing Sheet

FIG 1

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 26 base pairs
      (B) TYPE: nucleic acid
      (C) STRANDEDNESS: double
      (D) TOPOLOGY: linear    (ii) MOLECULE TYPE: DNA (genomic)

(xi) SEQUENCE DESCRIPTION: SEQ ID NO:1:

CATATTTACA ACCATGGCAC CACCTC                          26

(2) INFORMATION FOR SEQ ID NO:2:

(i) SEQUENCE CHARACTERISTICS:
      (A) LENGTH: 19 base pairs
      (B) TYPE: nucleic acid
      (C) STRANDEDNESS: double
      (D) TOPOLOGY: linear    (ii) MOLECULE TYPE: DNA (genomic)

(xi) SEQUENCE DESCRIPTION: SEQ ID NO:2:

CCACTGCGTT GGAATAGAC                                19

(2) INFORMATION FOR SEQ ID NO:3:

(i) SEQUENCE CHARACTERISTICS:
      (A) LENGTH: 22 base pairs
      (B) TYPE: nucleic acid
      (C) STRANDEDNESS: double
      (D) TOPOLOGY: linear    (ii) MOLECULE TYPE: DNA (genomic)

(xi) SEQUENCE DESCRIPTION: SEQ ID NO:3:

CTAAGCGYGA TGCBCMRTGG CG                              22

(2) INFORMATION FOR SEQ ID NO:4:

(i) SEQUENCE CHARACTERISTICS:
      (A) LENGTH: 20 base pairs
      (B) TYPE: nucleic acid
      (C) STRANDEDNESS: double
      (D) TOPOLOGY: linear    (ii) MOLECULE TYPE: DNA (genomic)

(xi) SEQUENCE DESCRIPTION: SEQ ID NO:4:

CGAATRTARA AATAGATCCG                               20

(2) INFORMATION FOR SEQ ID NO:5:

(i) SEQUENCE CHARACTERISTICS:
    (A) LENGTH: 1651 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:5:

| | | | | | |
|---|---|---|---|---|---|
| CTCGAGGAAC | ATGGTGGACC | ACGACACTCT | CGTCTACTCC | AAGAATATTC | AAAGATACAG | 60 |
| TCTCAGAAGA | CCAAAGGGCT | ATTGAGACTT | TCAACAAAG | GGTAATATCG | GAACCTCCT | 120 |
| CGGATTCCAT | TGCCCAGCTA | TCTGTCACTT | CATCAAAAGG | ACAGTAGAAA | AGGAAGGTGG | 180 |
| CACCTACAAA | TGCCATCATT | GCGATAAAGG | AAAGGCTATC | GTTCAAGATG | CCTCTGCCGA | 240 |
| CAGTGGTCCC | AAAGATGGAC | CCCCACCCAC | GAGGAGCATC | GTGGAAAAAG | AAGACGTTCC | 300 |
| AACCACGTCT | TCAAAGCAAG | TGGATTGATG | TGATATCTCC | ACTGACGTAA | GGGATGACGC | 360 |
| ACAATCCCAC | TATCCTTCGC | AAGACCCTTC | CTCTATATAA | GGAAGTTCAT | TTCATTTGGA | 420 |
| GAGGACACCA | AGCTTTTTAT | TTTTAATTTT | CTTTCAAATA | CTTCCACCAT | GCCACCACCT | 480 |
| CAAAGATTTA | GAGTTCAGTC | GAAAAACTAT | TTCCTCACTT | ATCCTCGTTG | CCCTATACCG | 540 |
| AAAGAAGAAG | TTCTTTCGCA | ACTTCAGAAG | ATTCATACAG | CCACGAATAA | AAAATTCATC | 600 |
| AAAGTCTGTG | AGGAACGTCA | CGAGAATGGT | GAACCTCATC | TTCATGCGCT | TATTCAATTC | 660 |
| GAAGGTAAAT | TCGTCTGCAC | AAATAAAAGA | TTGTTCGACC | TGGTATCCTC | AACCAGGTCA | 720 |
| GCACCTTTCC | ATCCGAACAT | TCAGGGAGCT | AAATCAAGTT | CAGACGTCAA | GGCATACATC | 780 |
| GACAAAGATG | GAGTCACAAT | CGAATGGGA | CAATTCCAAG | TCGACGGCAG | ATCTGCAAGA | 840 |
| GGAGGTCAGC | AGTCTGCCAA | CGACTCATAT | GCAAAGGCAT | TAAACGCAGA | TTCAATTGAA | 900 |
| TCTGCCTTGA | CAATATTGAA | GGAAGAACAA | CCGAAAGATT | ACGTCCTTCA | ACATCACAAC | 960 |
| ATCCGTTCTA | ATCTCGAACG | GATCTTCGTC | AAAGTGCCGG | AACCATGGGT | TCCTCCATTT | 1020 |
| CCGTTGTCAT | CATTCATCAA | TGTTCCGGTT | GTTATGCAAG | AATGGGTTGA | CGACTATTTC | 1080 |
| GGAAGGGGTT | CCGCTGCGCG | GCCGGAAAGA | CCTATTAGTA | TCATCGTCGA | AGGTGATTCA | 1140 |
| CGAACCGGAA | AGACAATGTG | GGCTCGTGCA | TTAGGACCAC | ATAATTATTT | GAGCGGTCAT | 1200 |
| TTGGACTTTA | ATTCACGTGT | CTATTCCAAC | GCAGTGGAAT | ACAACGTCAT | TGATGACATA | 1260 |
| AGCCCCAATT | ATTTGAAGTT | AAAGCACTGG | AAAGAACTAA | TTGGGGCACA | AAAGGACTGG | 1320 |
| CAATCTAACT | GTAAATATGG | AAAGCCGGTT | CAAATTAAAG | GAGGAATACC | ATCAATCGTG | 1380 |
| TTGTGCAATC | CAGGTGAGGG | TTCCAGTTAT | AAAGACTTCC | TCGACAAAGA | AGAAAACCGA | 1440 |
| GCTTTACACA | ACTGGACTAT | TCATAATGCG | ATCTTCGTCA | CCCTCACAGC | CCCCCTCTAT | 1500 |
| CAAAGCACAA | CACAGGATTG | CCAAACGTAG | AGCCATTCGT | CGACGACGCA | TTGACTTGAA | 1560 |
| CTGCGGCTGT | TCCATATTTT | ACCATATCAA | GTGCGCAGAT | CATGGATTCA | CGCACAGGGG | 1620 |
| AGAACATCAC | TGCGCATCAG | GCAGAGAATT | C | | | 1651 |

(2) INFORMATION FOR SEQ ID NO:6:

(i) SEQUENCE CHARACTERISTICS:
        (A) LENGTH: 1651 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

-continued

```
CTCGAGGAAC ATGGTGGACC ACGACACTCT CGTCTACTCC AAGAATATTC AAAGATACAG         60

TCTCAGAAGA CCAAAGGGCT ATTGAGACTT TTCAACAAAG GGTAATATCG GAACCTCCT         120

CGGATTCCAT TGCCCAGCTA TCTGTCACTT CATCAAAAGG ACAGTAGAAA AGGAAGGTGG        180

CACCTACAAA TGCCATCATT GCGATAAAGG AAAGGCTATC GTTCAAGATG CCTCTGCCGA        240

CAGTGGTCCC AAAGATGGAC CCCCACCCAC GAGGAGCATC GTGGAAAAAG AAGACGTTCC        300

AACCACGTCT TCAAAGCAAG TGGATTGATG TGATATCTCC ACTGACGTAA GGGATGACGC        360

ACAATCCCAC TATCCTTCGC AAGACCCTTC CTCTATATAA GGAAGTTCAT TTCATTTGGA       420

GAGGACACCA AGCTTTTTAT TTTTAATTTT CTTTCAAATA CTTCCACCAT GGCACCACCT        480

CAAAGATTTA GAGTTCAGTC GAAAAACTAT TTCCTCACTT ATCCTCGTTG CCCTATACCG       540

AAAGAAGAAG TTCTTTCGCA ACTTCAGAAG ATTCATACAG CCACGAATAA AAAATTCATC       600

AAAGTCTGTG AGGAACGTCA CGAGAATGGT GAACCTCATC TTCATGCGCT TATTCAATTC       660

GAAGGTAAAT TCGTCTGCAC AAATAAAAGA TTGTTCGACC TGGTATCCTC AACCAGGTCA       720

GCACCTTTCC ATCCGAACAT TCAGGGAGCT AAATCAAGTT CAGACGTCAA GGCATACATC       780

GACAAAGATG GAGTCACAAT CGAATGGGGA CAATTCCAAG TCGACGGCAG ATCTGCAAGA       840

GGAGGTCAGC AGTCTGCCAA CGACTCTATA TGCAAAGGCAT TAAACGCAGA TTCAATTGAA      900

TCTGCCTTGA CAATATTGAA GGAAGAACAA CCGAAAGATT ACGTCCTTCA ACATCACAAC       960

ATCCGTTCTA ATCTCGAACG GATCTTCGTC AAAGTGCCGG AACCATGGGT TCCTCCATTT      1020

CCGTTGTCAT CATTCATCAA TGTTCCGGTT GTTATGCAAG AATGGGTTGA CGACTATTTC      1080

GGAAGGGGTT CCGCTGCGCG GCCGGAAAGA CCTATTAGTA TCATCGTCGA AGGTGATTCA      1140

CGAACCGGAA AGACAATGTG GGCTCGTGCA TTAGGACCAC ATAATTATTT GAGCGGTCAT      1200

TTGGACTTTA ATTCACGTGT CTATTCCAAC GCAGTGGAAT ACAACGTCAT TGATGACATA      1260

AGCCCCAATT ATTTGAAGTT AAAGCACTGG AAAGAACTAA TTGGGGCACA AAAGGACTGG      1320

CAATCTAACT GTAAATATGG AAAGCCGGTT CAAATTAAAG GAGGAATACC ATCAATCGTG      1380

TTGTGCAATC CAGGTGAGGG TTCCAGTTAT AAAGACTTCC TCGACAAAGA AGAAAACCGA      1440

GCTTTACACA ACTGGACTAT TCATAATGCG ATCTTCGTCA CCCTCACAGC CCCCCTCTAT      1500

CAAAGCACAA CACAGGATTG CCAAACGTAG AGCCATTCGT CGACGACGCA TTGACTTGAA      1560

CTGCGGCTGT TCCATATTTT ACCATATCAA GTGCGCAGAT CATGGATTCA CGCACAGGGG      1620

AGAACATCAC TGCGCATCAG GCAGAGAATT C                                     1651
```

(2) INFORMATION FOR SEQ ID NO:7:

(i) SEQUENCE CHARACTERISTICS:
        (A) LENGTH: 2072 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:7:

```
CTCGAGGAAC ATGGTGGACC ACGACACTCT CGTCTACTCC AAGAATATTC AAAGATACAG         60

TCTCAGAAGA CCAAAGGGCT ATTGAGACTT TTCAACAAAG GGTAATATCG GAACCTCCT         120

CGGATTCCAT TGCCCAGCTA TCTGTCACTT CATCAAAAGG ACAGTAGAAA AGGAAGGTGG        180

CACCTACAAA TGCCATCATT GCGATAAAGG AAAGGCTATC GTTCAAGATG CCTCTGCCGA        240

CAGTGGTCCC AAAGATGGAC CCCCACCCAC GAGGAGCATC GTGGAAAAAG AAGACGTTCC        300
```

```
AACCACGTCT TCAAAGCAAG TGGATTGATG TGATATCTCC ACTGACGTAA GGGATGACGC      360

ACAATCCCAC TATCCTTCGC AAGACCCTTC CTCTATATAA GGAAGTTCAT TCATTTGGA      420

GAGGACACCA AGCTTTTTAT TTTTAATTTT CTTTCAAATA CTTCCACCAT GCCACCACCT      480

CAAAGATTTA GAGTTCAGTC GAAAAACTAT TTCCTCACTT ATCCTCGTTG CCCTATACCG      540

AAAGAAGAAG TTCTTTCGCA ACTTCAGAAG ATTCATACAG CCACGAATAA AAAATTCATC      600

AAAGTCTGTG AGGAACGTCA CGAGAATGGT GAACCTCATC TTCATGCGCT TATTCAATTC      660

GAAGGTAAAT TCGTCTGCAC AAATAAAAGA TTGTTCGACC TGGTATCCTC AACCAGGTCA      720

GCACCTTTCC ATCCGAACAT TCAGGGAGCT AAATCAAGTT CAGACGTCAA GGCATACATC      780

GACAAAGATG GAGTCACAAT CGAATGGGGA CAATTCCAAG TCGACGGCAG ATCTGCAAGA      840

GGAGGTCAGC AGTCTGCCAA CGACTCATAT GCAAAGGCAT TAAACGCAGA TTCAATTGAA      900

TCTGCCTTGA CAATATTGAA GGAAGAACAA CCGAAAGATT ACGTCCTTCA ACATCACAAC      960

ATCCGTTCTA ATCTCGAACG GATCTTCGTC AAAGTGCCGG AACCATGGGT TCCTCCATTT     1020

CCGTTGTCAT CATTCATCAA TGTTCCGGTT GTTATGCAAG AATGGGTTGA CGACTATTTC     1080

GGAAGGGGTT CCGCTGCGCG GCCGGAAAGA CCTATTAGTA TCATCGTCGA AGGTGATTCA     1140

CGAACCGGAA AGACAATGTG GGCTCGTGCA TTAGGACCAC ATAATTATTT GAGCGGTCAT     1200

TTGGACTTTA ATTCACGTGT CTATTCCAAC GCAGTGGAAT ACAACGTCAT TGATGACATA     1260

AGCCCCAATT ATTTGAAGTT AAAGCACTGG AAAGAACTAA TTGGGGCACA AAAGGACTGG     1320

CAATCTAACT GTAAATATGG AAAGCCGGTT CAAATTAAAG GAGGAATACC ATCAATCGTG     1380

TTGTGCAATC CAGGTGAGGG TTCCAGTTAT AAAGACTTCC TCGACAAAGA AGAAAACCGA     1440

GCTTTACACA ACTGGACTAT TCATAATGCG ATCTTCGTCA CCCTCACAGC CCCCCTCTAT     1500

CAAAGCACAA CACAGGATTG CCAAACGTAG AGCCATTCGT CGACGACGCA TTGACTTGAA     1560

CTGCGGCTGT TCCATATTTT ACCATATCAA GTGCGCAGAT CATGGATTCA CGCACAGGGG     1620

AGAACATCAC TGCGCATCAG GCAGAGAATT CCCGTTTTTA TTTGGGAGGT ACCAAATCCC     1680

CTTTATTTCA AGATAATGCG GGTGGAAGAT CCAGCATACA CACGGACAAG GATATACCAC     1740

ATCCAAATCA GGTTCAATCA CAACCTCAGG AAAGCACTGG ATCTCCACAA AGCATTCCTG     1800

AACTTCCAAG TCTGGACGAC ATCGATTCAA GCTTCTGGGA CGACATATTT AAATAGATTT     1860

AGACATTTGG TTTTATTGTA TTTACATAGG TTAGGCGTAA TAGGAATAAA CAATGTAATT     1920

CGAGCTGTTC AGTTCGCAAC AGACAAATTA TATGTAAATA CTGTGCTTGA GAATCATGAA     1980

ATAAAATATA AATTTTATTA ATTGGTTATC GAATCATAGA AATAGATCCG AATTTTCAAT     2040

GTCGCATATA CAGGGTTAGA GGCATGTCTA GA                                   2072
```

(2) INFORMATION FOR SEQ ID NO:8:

(i) SEQUENCE CHARACTERISTICS:
        (A) LENGTH: 1894 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:8:

```
CTCGAGGAAC ATGGTGGACC ACGACACTCT CGTCTACTCC AAGAATATTC AAAGATACAG       60

TCTCAGAAGA CCAAAGGGCT ATTGAGACTT TCAACAAAG GGTAATATCG GAACCTCCT       120

CGGATTCCAT TGCCCAGCTA TCTGTCACTT CATCAAAAGG ACAGTAGAAA AGGAAGGTGG      180
```

-continued

```
CACCTACAAA TGCCATCATT GCGATAAAGG AAAGGCTATC GTTCAAGATG CCTCTGCCGA       240

CAGTGGTCCC AAAGATGGAC CCCCACCCAC GAGGAGCATC GTGGAAAAAG AAGACGTTCC       300

AACCACGTCT TCAAAGCAAG TGGATTGATG TGATATCTCC ACTGACGTAA GGGATGACGC       360

ACAATCCCAC TATCCTTCGC AAGACCCTTC CTCTATATAA GGAAGTTCAT TTCATTTGGA       420

GAGGACACCA AGCTTTTTAT TTTTAATTTT CTTTCAAATA CTTCCACCAT GCCACCACCT       480

CAAAGATTTA GAGTTCAGTC GAAAAACTAT TTCCTCACTT ATCCTCGTTG CCCTATACCG       540

AAAGAAGAAG TTCTTTCGCA ACTTCAGAAG ATTCATACAG CCACGAATAA AAAATTCATC       600

AAAGTCTGTG AGGAACGTCA CGAGAATGGT GAACCTCATC TTCATGCGCT TATTCAATTC       660

GAAGGTAAAT TCGTCTGCAC AAATAAAAGA TTGTTCGACC TGGTATCCTC AACCAGGTCA       720

GCACCTTTCC ATCCGAACAT TCAGGGAGCT AAATCAAGTT CAGACGTCAA GGCATACATC       780

GACAAAGATG GAGTCACAAT CGAATGGGGA CAATTCCAAG TCGACGGCAG ATCTGCAAGA       840

GGAGGTCAGC AGTCTGCCAA CGACTCATAT GCAAAGGCAT TAAACGCAGA TTCAATTGAA       900

TCTGCCTTGA CAATATTGAA GGAAGAACAA CCGAAAGATT ACGTCCTTCA ACATCACAAC       960

ATCCGTTCTA ATCTCGAACG GATCTTCGTC AAAGTGCCGG AACCATGGGT TCCTCCATTT      1020

CCGTTGTCAT CATTCATCAA TGTTCCGGTT GTTATGCAAG AATGGGTTGA CGACTATTTC      1080

GGAAGGGGTT CCGCTGCGCG GCCGGAAAGA CCTATTAGTA TCATCGTCGA AGGTGATTCA      1140

CGAACCGGAA AGACAATGTG GGCTCGTGCA TTAGGACCAC ATAATTATTT GAGCGGTCAT      1200

TTGGACTTTA ATTCACGTGT CTATTCCAAC GCAGTGGAAT ACAACGTCAT TGATGACATA      1260

AGCCCCAATT ATTTGAAGTT AAAGCACTGG AAAGAACTAA TTGGGGCACA AAAGGACTGG      1320

CAATCTAACT GTAAATATGG AAAGCCGGTT CAAATTAAAG GAGGAATACC ATCAATCGTG      1380

TTGTGCAATC CAGGTGAGGG TTCCAGTTAT AAAGACTTCC TCGACAAAGA AGAAAACCGA      1440

GCTTTACACA ACTGGACTAT TCATAATGCG ATCTTCGTCA CCCTCACAGC CCCCCTCTAT      1500

CAAAGCACAA CACAGGATTG CCAAACGTAG AGCCATTCGT CGACGACGCA TTGACTTGAA      1560

CTGCGGCTGT TCCATATTTT ACCATATCAA GTGCGCAGAT CATGGATTCA CGCACAGGGG      1620

AGAACATCAC TGCGCATCAG GCAGAGATTC AAGCTTCTGG GACGACATAT TTAAATAGAT      1680

TTAGACATTT GGTTTTATTG TATTTACATA GGTTAGGCGT AATAGGAATA AACAATGTAA      1740

TTCGAGCTGT TCAGTTCGCA ACAGACAAAT TATATGTAAA TACTGTGCTT GAGAATCATG      1800

AAATAAAATA TAAATTTTAT TAATTGGTTA TCGAATCATA GAAATAGATC CGAATTTTCA      1860

ATGTCGCATA TACAGGGTTA GAGGCATGTC TAGA                                 1894
```

TRANS-DOMINANT INHIBITION OF GEMINIVIRAL DNA REPLICATION BY GEMINIVIRUS REP GENE MUTANTS

CROSS-REFERENCE TO RELATED APPLICATIONS

This application claims priority to U.S. Provisional Application No. 60/044,925 filed Apr. 25, 1997.

STATEMENT REGARDING FEDERALLY SPONSORED RESEARCH OR DEVELOPMENT

Not applicable.

BACKGROUND OF THE INVENTION

Geminiviruses are plant pathogenic, single stranded DNA viruses that cause major losses in a number of important crops throughout the world. In many areas, geminiviruses are the greatest constraint on production of important crops, including cassava, beans, cowpeas, peppers, tomatoes, and cotton. In the continental U.S., geminiviruses cause severe problems in tomatoes, peppers, melons, and beans. Bean golden mosaic virus (BGMV) is a typical bipartite, whitefly-transmitted geminivirus that causes severe disease in beans (*Phaseolus vulgaris*) in the Western Hemisphere. In Latin America, where beans are an important food staple, BGMV infection of bean plants is the major cause of reduced bean production. BGMV also causes substantial crop loss in pole beans in Florida.

Geminiviruses replicate via a rolling circle type of mechanism (Saunders et al., *Nucleic Acids Res.* 19:2325–2330, 1991; Stenger, et al. *Proc. Natl. Acad. Sci. USA* 88:8029–8033, 1991) similar to bacteriophages such as φ X174. A geminivirus gene known as the rep gene encodes a complex, multifunctional protein, which acts as a rolling circle initiator protein analogous to protein A of φ X174. The rep gene is the only geminiviral gene necessary for viral replication (Elmer., *Nucleic Acid Res.* 16:7043–7060, 1988; Etessami et al., *J. Gen. Virol.* 72:1005–1012, 1991; Hanley-Bowdoin et al., *Proc. Natl. Acad. Sci. USA* 87:1446–1450, 1990).

The origin of replication (ori) of geminiviruses is characterized by a series of direct repeat sequences located between the transcription and translation start sites for the rep gene (Eagle et al., *Plant Cell* 6:1157–1170, 1994; Faria et al., *Phytopathology* 84:7043–7060, 1994; Fontes et al., *J. Biol. Chem.* 269:8459–8465, 1994). The Rep proteins from tomato golden mosaic virus (TGMV) and BGMV-GA (Guatemalan isolate) have been shown to bind to these direct repeats (Chapter V; Fontes et al., *Plant Cell* 4:597–608, 1992). The interaction between the Rep protein and the direct repeats is necessary for replication and auto-regulation of the rep gene (Eagle et al., *Plant Cell* 6:1157–1170, 1994; Fontes et al., *Plant Cell* 6:405–416, 1994). The direct repeats are generally conserved in position but vary in sequence between different phylogenetic clusters of geminiviruses. The interaction between the Rep protein and the ori is highly specific. Rep proteins from BGMV-GA and TGMV are able to interact with their cognate ori sequences but not to heterologous cri sequences (Chapter V; Fontes, et al. *J. Biol. Chem.* 269:8459–8465, 1994).

There exists no known natural resistance to geminiviruses. Efforts to develop geminivirus-resistant beans and tomatoes have been underway for about two decades. These breeding programs have been generally unsuccessful (Beebe., *Crop Science* 35:1178–1183, 1995; Morales et al., *Euphytica* 52:113–118, 1991). The tyl gene, which confers partial resistance to TYLCV, has been identified in wild tomato species (Nateshan et al., In *Bemisia* 1995: *Taxonomy. Biology. Damage, Control and Management* D. G. a. R. T. Mayer, Ed., pp 369–377. Intercept Ltd.; ZAMIR 1994). However, the tyl gene is not effective against other tomato-infecting geminiviruses such as ToMoV and has been difficult to introgress into commercial cultivars. A source of partial BGMV resistance, a recessive gene (bgm1) from breeding A429. has been identified for beans. The bgm1 gene has recently been incorporated into pole beans in Florida and into small red beans in Honduras. It is not known if the bgm 1 gene will confer resistance to other bean-infecting geminiviruses such as BGMV-BZ (Brazil), bean dwarf mosaic virus (BDMV), or bean calico mosaic virus.

The lack of natural resistance to geminiviruses has led to attempts to engineer resistance, particularly through the use of virus-derived resistance strategies (Frischmuth and Stanley, *Sem. Virol.* 4:329–337, 1993). Because the rep gene is the only gene necessary for geminiviral DNA replication (Hanley-Bowoin et al. *Proc. Natl. Acad. Sci. USA* 87:1446–1450, 1990), it is an attractive target for engineering geminivirus resistance.

What is needed in the art is a method of interfering with the function of geminiviral rep genes so as to inhibit replication of geminivirus in plants.

BRIEF SUMMARY OF THE INVENTION

The present invention is a genetic construct comprising a plant promoter operably connected to a trans-dominant inhibitor of the geminiviral rep gene.

The present invention is also a method of protecting plants against geminivirus infection by introducing into the plant genome an expressible trans-dominant inhibitor of geminiviral replication.

The present invention is a transgenic plant, plant cell, or plant seed comprising in its genome a genetic construct comprising a plant promoter operably connected to a trans-dominant inhibitor of the geminiviral rep gene.

It is an object of the present invention to reduce the loss of production in crops that are normally susceptible to geminiviruses.

It is another object of the invention to provide a genetic construct comprising an expressible trans-dominant inhibitor of the geminiviral rep gene that, when expressed in a plant or plant cells, prevents replication of a geminivirus in the plant.

Other objects, advantages, and features of the present invention will become apparent from the following specification.

DETAILED DESCRIPTION OF THE INVENTION

One aspect of the present invention is a transgenic plant, plant cell, or plant seed comprising in its genome a genetic construct comprising a plant promoter operably connected to a trans-dominant inhibitor of a geminiviral rep gene.

By "trans-dominant inhibitor" it is meant a DNA sequence that inhibits the function of a geminiviral rep gene when the inhibitor is present in the plant genome in trans. A trans-dominant inhibitor is preferably geminiviral rep gene bearing a mutation that causes the expression of a mutant rep protein which interferes with replication of an infecting geminivirus of the same or different viral strain. Suitable locations for such mutations include the NTP-binding region, the DNA-nicking region and other functionally important domains of the rep gene.

The examples below describe the construction of vectors comprising trans-dominant inhibitors derived from the BGMV rep gene. It is expected that one of ordinary skill in the art, using the guidance provided by the examples below, could readily develop trans-dominant inhibitors of other geminivirus rep genes. Consequently, it is anticipated that the present invention could be practiced using any geminivirus. However, it has also been discovered that not only does the mutant rep gene confer resistance to the geminivirus from which it was developed, but it can confer resistance to a broad spectrum of diverse geminiviruses.

In a preferred embodiment, the genetic construct comprises an ac3 gene sequence in addition to the mutant rep gene. As the examples below demonstrate, the presence of a sequence that overlaps the ac3 gene enhances the efficiency and broadens the specificity of mutant rep-mediated trans-dominance.

To be expressed in plants, genes must be activated or driven by a promoter effective in plant cells to initiate transcription. Many such promoters, and the techniques for assembling and using them, are known. The CaMV 35S promoter, which was employed in the genetic constructs described in the examples, is an exemplary constitutive promoter used since it is known to function in a wide variety of plants. Any promoter that is functional in the plant into which the construct will be introduced may be used to create a genetic construct to be used in the practice of the present invention. Suitable promoters may include other constitutive promoters, tissue-specific promoters, developmental stage-specific promoters, and inducible promoters. Promoters may also contain transcriptional or translational enhancer sequence elements that improve the overall efficiency of gene expression in the plant.

The present invention is also a method for preventing the replication of a geminivirus in a plant comprising the steps of providing a genetic construct comprising a plant promoter operably connected to a trans-dominant inhibitor of a geminiviral rep gene and introducing the vector into the plant.

The lack of natural sources of resistance sufficient for control of diseases caused by geminiviruses has led to the exploration of engineered resistance strategies (Frischmuth and Stanley, *Sem. Virol.* 4:329–37, 1993). We chose to target the rep gene for engineering resistance, since it is the only geminiviral gene necessary for DNA replication (Hanley-Bowdoin et al., *Proc. Natl. Acad. Sci. USA* 87:1446–1450, 1990; Hanson et al., *Viroloay* 211:1–9, 1995). We have previously reported genetic studies which demonstrated that the putative DNA-nicking and NTP-binding domains, which are conserved in the rep gene of every geminivirus, are necessary for geminiviral DNA replication (Hanson et al., *Virology* 211:1–9 1995; Hoogstraten et al., *MPMI* 9:594–599, 1996). Experiments testing the ability of rep genes containing lethal mutations within these domains to function as trans-dominant inhibitors of geminiviral replication are reported in this chapter. We also demonstrate that sequences which overlap the ac3 gene, enhance and broaden the specificity of rep-mediated trans-dominance.

The ability of mutant rep genes to trans-dominantly inhibit geminiviral replication was tested using a transient assay where rep expression plasmids were co-inoculated with cloned geminiviral DNA-As into NT-1 suspension cells. A transient assay for testing transgene effects was used, rather than constructing transgenic plants, for several reasons. It would have been difficult or impossible to compare results between different constructs in transgenic plants since differences in transgene expression due to copy number and/or position effects can greatly influence transgene expression and activity in transgenic plants (Goodwin et al., *Plant Cell* 8:95–105, 1996). Also, the large number of constructs that were tested precluded the use of transgenic plants, given the time and resources required to produce transgenic plants. Gene dosage and timing of gene expression relative to geminiviral inoculation are two important parameters that are different between transgenic and transient systems. Since one goal of this research was to evaluate potential geminivirus resistance gene constructs, we attempted to compensate for differences in these characteristics between our transient assay and transgenic models. Every cell in a transgenic plant should contain the transgene, while it is unlikely that every cell will take up the transient expression vector after inoculation. Also, trans-gene expression should be at steady state levels at the time of geminiviral inoculation in our transient assay. The high ratio of rep trans-expression vector to DNA-A in the inoculum is intended to minimize the population of cells receiving DNA-A but not the rep trans-expression vectors, and to compensate for the temporal differences in gene expression by providing high initial expression of the trans-genes in this transient assay.

The results below show that the wild type rep gene from BGMV-GA is sufficient for replication of BGMV-GA DNA-B in NT-1 suspension cells and that the ac3 gene enhances replication. These data indicate that functional Rep and Ac3 proteins are produced after inoculation of NT-1 suspension cells with the rep trans-expression vectors used and are consistent with a number of previous studies characterizing the roles of rep and ac3 genes in geminiviral DNA replication (Hanson et al., *Virology* 211:1–9, 1995; Hoogstraten et al., *MPMI* 9:594–599, 1996; Sunter et al., *Virology* 179:69–77, 1990). Trans-expressed mutant rep genes significantly inhibited replication of BGMV-GA DNA-A, and sequences from 1,041 to 1,472. which contain the ac3 gene and putative complementary sense transcription termination signals, increased trans-dominant activity. The complete ac3 gene was not required for high level trans-dominance, since mutant rep genes expressed from the pTrepΔE/CX vectors (described below), which have ac3 gene codons 17–84 deleted (pTrep23ΔE/CX vectors), were also highly trans-dominant. These results show that sequences from 1,041–1,299 were sufficient for enhancing the efficiency of trans-dominant rep genes.

Mutant rep genes derived from BGMV-GA were tested for the ability to interfere with the replication of several heterologous geminiviruses, which cause severe losses on beans in Latin America, including BGMV-DR, BGMV-BZ, and BDMV. BGMV-GA and BGMV-DR. BGMV-GA and BGMV-DR are very closely related since the DNA-As are ~97% identical at the sequence level, the direct repeat sequences bound by the Rep protein are identical, and BGMV-GA and BGMV-DR can infect plants as pseudo recombinants comprised of DNA-A from one virus and DNA-B of the other (Faria et al., *Phytopatology* 84:321–329, 1994). BGMV-GA is not closely related to BMGV-BZ and BDMV, both of which are only about 75% identical to BGMV-GA at the sequence level and unable to form pseudo recombinants with BGMV-GA (Faria et al.,

*Phytopatology* 84:321–329, 1994). Trans-dominant rep gene mutants expressed as rep genes only (pTrepX vectors) were able to inhibit replication of BGMV-GA and BGMV-DR but not BGMV-BZ and BDMV. However, replication of DNA-As from BGMV-BZ and BDMV was inhibited by rep mutants Y103F and D262R when expressed from the pTrepΔE/CX vector. These results demonstrate that mutant rep genes can inhibit replication of geminiviruses other than those from which they were generated.

The results of these experiments supports some conclusions as to the mechanism of trans-dominance. Trans-expression of wild type and ATG- rep genes from pTrepX and pTrep23X vectors did not inhibit replication of BGMV-GA DNA-A indicating that expression of non-functional Rep protein is necessary and sufficient for trans-dominance and that RNA mediated mechanisms do not contribute to trans-dominance. These results also show that the truncated ac2 gene contained in the pTrepX, and the full-length wild type ac2 and ac3 genes present in pTrep23 do not mediate trans-dominance.

Experiments testing the ability of trans-expressed rep gene mutants indicated that trans-dominance is primarily mediated by Rep protein/ori DNA interactions and that a secondary, less efficient mechanisms, can also mediate trans-dominance. Mutant rep genes expressed from pTrepX vectors were able to inhibit replication of DNA-As from BGMV-GA and BGMV-DR but not BGMV-BZ or BDMV. Interactions between the Rep protein and ori are required for replication and auto-expression of the rep gene at the level of transcription (Eagle et al., *Plant Cell* 6:1157–1170, 1994; Fontes et al., *J. Biol. Chem.* 269:8459–8465, 1994). Geminiviruses have a high degree of replication specificity, which correlates with Rep protein binding specificity to ori DNA (Fontes et al., *J. Biol. Chem.* 269:8459–8465, 1994). Since BGMV-DR can form pseudo recombinants with BGMV-GA while BGMV-BZ and BDMV cannot, it is likely that the Rep protein of BGMV-GA can interact with the ori of BGMV-DR but not with or is of BGMV-BZ or BDMV. Recent in vitro DNA-binding results and chimeric replicon studies have shown that the Rep protein of BGMV-GA does interact with the ori of BGMV-DR but not with the or is of BGMV-BZ or BDMV. The correlation between replication specificity, in vitro DNA-binding, and trans-dominant activity indicates that trans-dominance is primarily mediated by Rep protein/ori DNA interactions. Interactions between a nonfunctional Rep protein and the ori could lead to trans-dominance by preventing expression of the viral rep gene at the level of transcription and/or by preventing initiation of replication at the ori.

The addition of sequences containing all or part of the ac3 gene, and associated putative transcriptional termination signals, in the rep trans-expression vectors increased the efficiency of trans-dominance. This effect occurred with both the full-length ac3 gene (BGMV-GA DNA-A nucleotide 1,041–1,472) and a non-functional ac3 gene, which had the codons for amino acids 18–74 deleted (BGMV-GA DNA-A nucleotides 1,041–1,299). In contrast, the full-length ac3 gene was able to increase the efficiency of rep gene-mediated replication while the truncated ac3 gene was not. Mutations in the start codon of the rep gene in pTrep and pTrep23 abolished trans-dominant activity from these constructs, showing that these sequences enhance the activity of trans-dominant rep genes, but do not suppress geminiviral replication on their own. In addition to enhancing the activity of trans-dominant rep gene constructs, sequences containing a truncated ac3 gene also broadened the specificity of trans-dominant rep genes. Replication of DNA-As from BGMV-BZ and BDMV was inhibited by rep gene mutants Y103F and D262R when expressed from pTrep23Δ/E/CX but not when these mutants were expressed from pTrepX, which lacks these sequences. It is not clear if broad-spectrum resistance is mediated by the same mechanisms that increases the efficiency of trans-dominance, or by the truncated AC3 protein encoded by the pTrep23ΔE/CX vectors.

The finding that BGMV-BZ and BDMV DNA-A replication was inhibited by mutant rep genes from BGMV-GA expressed in conjunction with sequences 1,299–1,041 shows that a second mechanisms, which appears to be independent of Rep protein/ori DNA interactions, can also mediate trans-dominance. Based on the current understanding of geminiviral replication, these are several potential mechanisms which could explain the observed broad-spectrum trans-dominant inhibition of geminiviral replication. The requirement for Rep protein expression and independence of DNA-binding specificity indicates that protein/protein interactions probably mediate broad-spectrum trans-dominance. The Rep protein of BGMV-GA has been shown to form and bind to ori DNA as multimeric complexes in vitro. The Rep proteins of TGMV and BGMV were shown to form homo- and hetero-multimers and interact with Ac3 protein from TGMV in vitro (Settlage et al., *J. Virology* 70:6790–6795, 1996). Rep protein is also expected to interact with host factors to facilitate replication (Nagar et al., *Plant Cell* 7:705–719, 1995; Xie et al., *EMBO J.* 14:4073–4082, 1995). Interactions between nonfunctional Rep protein and viral expressed Rep protein or host factors that are necessary for geminiviral replication could inhibit replication by preventing the formation of active replication complexes in infected cells independent of ori-binding activity. Since the sequences from BGMV-GA DNA-A nucleotide 1,299–1,041 contain putative transcription signals, it is possible that these sequences enhance the activity of trans-dominant rep mutants by increasing the level of Rep protein expression via increased mRNA accumulation. Increased accumulation of nonfunctional Rep protein would be expected to enhance trans-dominance mediated by Rep protein/ori DNA interactions, which was observed. Increased accumulation of nonfunctional Rep protein would also allow observation of trans-dominance mediated by less efficient mechanisms. Thus, the data presented are consistent with a model where highly specific Rep protein/ori DNA interactions are the primary mechanisms of trans-dominance, and where less specific protein/protein interactions contribute secondarily to trans-dominance. It is also possible that the AC3 protein acts synergistically with trans-dominant Rep proteins to enhance protein/protein interactions that cause trans-dominance, though this is considered unlikely since the ac3 gene was present in all DNA-As while these sequences only enhanced trans-dominance when they were present in cis to the mutant rep genes. The data presented here does not exclude the possibility that the truncated ac3 gene produces a protein which has broad-spectrum trans-dominant activity or broadens the specificity of trans-dominant rep genes, possibly by altering the DNA-binding specificity of trans-dominant Rep proteins or by acting synergistically with trans-dominant Rep protein to form non-functional replication complexes. Regardless of whether this model is correct, the efficacy of this strategy to inhibit viral replication is clear.

Not all mutations that abolish rep gene function were trans-dominant. No significant inhibition of BGMV-GA DNA-A replication was caused by any rep trans-expression vector containing a E221R mutation in the rep gene. The E221R mutation in the rep gene of BGMV-GA was previously shown to have a temperature sensitive phenotype for replication (Hanson et al., *Virology* 211:1–9, 1995). All experiments reported here were performed at 28°, a non-emissive temperature for this mutation. It is possible that this mutation creates an unstable protein at the non-permissive temperature, which would explain the lack of trans-dominant activity by rep genes containing this mutation. Instability of Rep proteins containing the E221R mutation could also explain the lack of trans-dominance from rep genes with both the E221R and K228H mutations. This possible explanation is consistent with our model which proposes that the Rep protein mediates trans-dominant suppression of geminiviral DNA replication. Empirical testing in the NT-1 model system can be used to test any proposed rep mutant for ones which are trans-dominant to inhibit viral replication.

The data presented compliment and extend several other studies examining the ability of trans-expressed rep genes to interfere with geminiviral replication. Truncated rep genes from African cassava mosaic virus (ACMV) and TYLCV-SAR have been shown to interfere with geminiviral replication in transgenic *N. benthamiana* plants (Hong and Stanley, *MPMI* 9:219–225, 1996; Noris et al., *Virology* 224:130–138, 1996). Though no immune lines were discovered, several lines with high levels of resistance were identified in each experiment. In both cases, the truncated rep gene mutants which interfered with replication coded for Rep proteins that contained the ori DNA-binding domain but lacked the NTP-binding domain. Plants with resistance to ACMV were completely susceptible to TGMV and beet curly top geminivirus, which is consistent with our hypothesis that Rep protein ori DNA interactions are the primary mechanism of trans-dominance. The TYLCV resistant plants were not tested for resistance to heterologous geminiviruses (Noris et al., *Virology* 224:130–138, 1996). Sequences analogous to BGMV-GA nucleotide 1,041–1,299 were not included in any of the constructs used in these experiments.

The conservation of the DNA-nicking and NTP-binding domains in all geminivirus rep genes indicates that this approach may be useful in generating resistance genes to any geminivirus. In addition to the results reported here, similar rep gene mutants from BGMV-BZ are trans-dominant inhibitors of BGMV-BZ replication in the NT-1 suspension cell system. Transgenic tomatoes have also been produced by others which express trans-dominant ToMoV rep mutants which are resistant to ToMoV when challenged by inoculation with the natural insect vector, Bemisia tabaci. All ToMoV resistant plants tested are susceptible to the unrelated geminivirus TYLCV-EG (Egyptian isolate of TYLCV). The finding that trans-dominant rep genes from BGMV-GA can interfere with replication of heterologous geminiviruses, when expressed in conjunction with sequences which overlap the ac3 gene, is important since the known diversity of geminiviruses on any given crop may be a limiting factor in successful application of narrow-spectrum resistance genes.

In the examples below, the trans-dominant inhibitor was introduced by means of electroporation into tobacco cells grown in suspension culture. Other methods of transformation may be used in the practice of the present invention. For example, one could employ Agrobacterium-mediated transformation, which is known to work well with all dicot plants and some monocots. Transgenic plants may obtained by particle bombardment, direct gene injection, or by any other method of plant transformation know to one skilled in the art of plant molecular biology. The experience to date in the technology of plant genetic engineering is that the method of gene introduction is not of particular importance in the phenotype achieved in the transgenic plant.

The nonlimiting examples that follow are intended to be purely illustrative.

EXAMPLES

Materials and Methods
Cloned Geminivirus DNAs

Previously described infectious clones were used in all experiments, pGAA2 (Hanson et al., *Virology* 211:1–9, 1995) and pGAB1 (Gilbertson et al., *Phytopatology* 81:980–985, 1991) for BGMV-GA DNA-A and DNA-B respectively, pBZAl for DNA-A of BGMV-BZ (Gilbertson et al., *Phytopatology* 81:980–985, 1991), and pBDA1 for DNA-A of BDMV (Gilbertson et al., *Phytopathology* 81:980–985, 1991). The viral DNA inserts were excised from plasmid vectors using suitable restriction enzymes (SpeI for pGAA2. BamHI for pGAB1. HindIII pBZA1. and BglII for pBDA1). Following digestion with restriction enzymes, the DNA, which comprised linear, unit length genomic components, was extracted with phenol/chloroform/isoamyl alcohol (25:24:1) and precipitated with ethanol. The DNA concentration of each sample was determined and adjusted to 1 µg/µl. The DNA was inoculated into plant cells by electroporation.

Construction of Rep Gene trans-expression Vectors

Figure 1:
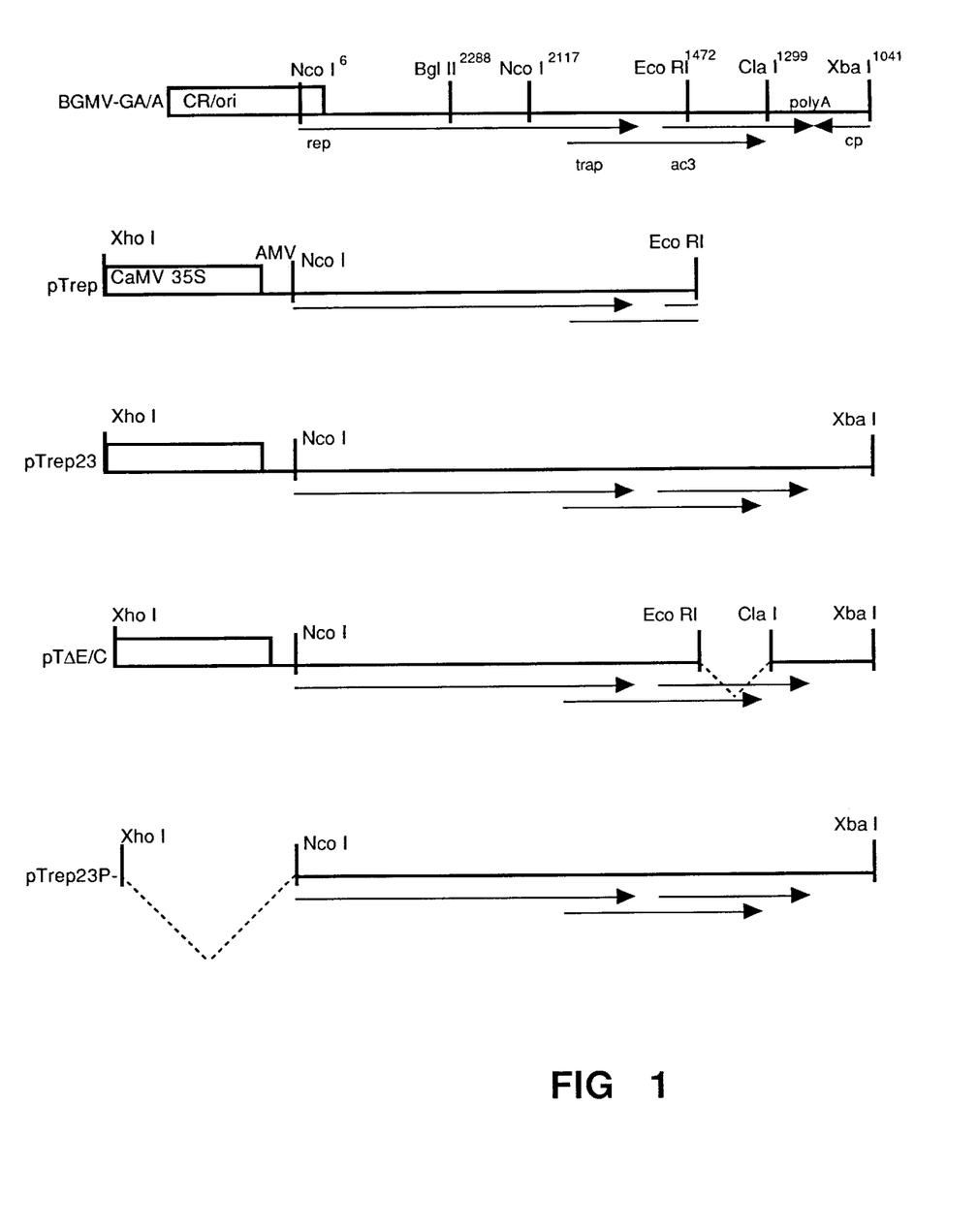
FIG. 1. Shows maps of rep gene trans-expression vectors.

Vectors constructed for transient expression of the NTP-binding and DNA-nicking domain mutants of rep protein in plant cells were derived from the rep expression vector pWRG2288 (gift from D. R. Russell, Agracetus Inc.). This plasmid contains the rep gene of BGMV-GA cloned downstream of the CaMV 35S promoter and an alfalfa mosaic virus (AMV) leader sequence (D. R. Russell, personal communication). An EcoRI/XhoI fragment containing the 35S-rep gene cassette was moved into pBSII-KS+ (pBS, Stratagene, La Jolla, Calif.) creating the rep gene expression vector pTrep (FIG. 1). A DNA sequence for the EcoRI/XhoI fragment from pWRG 2288 is set forth as SEQ ID NO:5 below. The pTrep plasmid codes for the entire rep gene, the n-terminal 60% (105 codons) of the trap gene and the first 16 codons of the ac3 gene. NTP-binding domain mutations were engineered into pTrep by cloning a BglII/EcoRI fragment from mutant DNA-As (Hanson et al., 1995) into pTrep in place of the wild type Bgl/IIEcoRI fragment. These manipulations, and the construction of the other plasmids used in the examples below are illustrated in FIG. 1. The resulting clones contain CaMV-35S promoter driven rep genes containing NTP-binding domain mutations and were designated pTrepX where X specifies mutations in the rep gene. Site-directed mutagenesis was used to engineer an NcoI site in the start codon of the rep gene in pTrep, to make pTrepN, to facilitate cloning of the DNA-nicking domain mutants. The sequence of pTrepN is set forth as Seq ID NO:6 below. In FIG. 1, the locations of site-directed mutagenesis are indicated by an asterisk. This mutation (CCATGC to CCATGg) changes the second codon of the rep protein from proline to alanine. This change was also made in wild type DNA-A(pGAA2N) and had no detectable effect on replication or infectivity (Data not shown). DNA-As containing DNA-nicking domain mutations were amplified by PCR from mutant DNA-As (Hoogstraten et al., *MPMI* 9:594–599, 1996) using primers Prep9-Nco (CATATTTACAACCATGGCACCACCTC) (SEQ ID NO:1) and Pav1885 (CCACTGCGTTGGAATAGAC) (SEQ ID NO:2). Primer Prep9-Nco contains mismatches around the start codon for rep gene (nt 6-3), and changes the sequence from ATATGCC to ccATGgC, thereby creating an NcoI site which matches the engineered Nco I site in pTrepN. The PCR products were digested with BglII and NcoI and cloned into pTrepN in place of the wild type BglII/NcoI fragment.

Rep trans-expression vectors containing the ac3 gene were constructed by cloning of an EcoRI/XbaI fragment from pGA RepZN, which contains rep/trap/ac3 cassette with an engineered XbaI site at position 1,041. The resulting clones contained a contiguous rep/trap/ac3 cassette, identical to that of BGMV-GA DNA-A, and were designated as pTrep23 (wild type rep sequence) (SEQ ID NO:7) or pTrep23X where X indicates mutations within the rep gene. The pTrep23 vectors also contain a canonical polyadenylation signals (AATAAA) which overlap the ends of the ac3 and cp genes (nt positions 1,125–1,130 and 1,137–1,142 in BGMV-GA DNA-A). A third series of rep trans-expression vectors was constructed where the EcoRI/ClaI sequences were deleted from pTrep23X vectors by digestion with both enzymes, filling in with T4 DNA polymerase, and self ligation (FIG. 1). DNA sequence analysis showed that all clones filled in completely, creating an in frame deletion in the ac3 gene which removes codons 17–83 and inserts two nonsense codons at codon positions 17 and 18 in all pTrep23ΔE/CX clones (SEQ ID NO:8). This series of clones was designated as ptrepΔE/CX where X denotes mutations within the rep gene.

The CaMV 35S promoter was removed from pTrep23N by digestion with XhoI and partial digestion with NcoI, followed by filling in of the overhangs with T4 DNA polymerase and self ligation to make pTrep23P-. Site-directed mutagenesis was used to change the rep gene start codon in pTrep, pTrep23. and pTrep32ΔE/C from ATG to ATC to make pTrepATG-, pTrep23ATG-, and pTrep23ΔE/CATG-.

Analysis of Geminiviral DNA Replication in NT-1 Suspension Cells

NT-1 (*Nicotiana tabacum*) suspension cells were maintained and inoculated by electroporation as previously described (Hanson et al., 1995). All inoculations were performed with a total of 100 μg of DNA. All treatments were replicated two or three times within each experiment to control for variability between inoculations. Inoculated NT-1 suspension cells were incubated at 28° in the dark in all experiments. Cells were harvested 72 hr. after inoculation and stored at –80° until analyzed. Total DNA was extracted from harvested cells as previously described (Hanson et al., 1995).

The ability of rep trans-expression vectors to replicate BGMV-GA DNA-B was tested by inoculating NT-1 suspension cells with 5 μg each of linearized BGMV-GA DNA-B and 95 μg of the indicated rep gene trans-expression plasmid or 20 μg DNA-A plus 75 μg of sheared salmon sperm DNA (Sigma Chemical Co., St. Louis, Mo.). The effect of trans-expressed rep gene on replication of geminiviral DNA-As was determined by co-inoculating NT-1 suspension cells with the indicated amounts of DNA-A (1 to 10 μg) and rep trans-expression vectors (90 to 99 μg) as indicated.

Replication products were detected by Southern analysis or by polymerase chain reaction (PCR) as previously described (Hanson et al., 1995). For Southern analysis, 1 μg of total DNA was digested with 2 units of DpnI overnight at 37° to digest residual inoculum DNA. In most experiments, a second enzyme was also used, which digests the geminiviral DNA at a single site to convert supercoiled and open circular dsDNAs into a single band of linear dsDNA to simplify quantification. NcoI was used for DNA-As of BGMV-GA and BGMV-DR while BglII was used for DNA-As of BGMV-BZ and BDMV, and DNA-B of BGMV-GA. Digested DNAs were resolved on 1% agarose gels (Seakem LE, FMC Bioproducts, Rockland, Me.) and blotted onto positively charged nylon membranes (Zeta bind, Cuno Inc., Meriden, Conn; or Qiabrane plus, Qiagen inc., Chatsworth, Calif.). $^{32}P$ labeled probes were produced by random hexamer labeling of cp gene sequences amplified from DNA-A by PCR with primers PGVvCP (CTAAGCGYGATGCBCMRTGGCG) (SEQ ID NO:3) and PGVcCP (CGAATRTARAAATAGATCCG) (SEQ ID NO:4). An NcoI fragment corresponding to nucleotide 976–1,837 was used as a probe for BGMV-GA DNA-B. Hybridizations were performed in the presence of 30% formamide as previously described (Gilbertson et al., 1991b). Probes blots were exposed to XAR-5 x-ray film (Kodak) for 2–120 hr. as necessary to obtain exposures appropriate for quantification. Southern blots were quantified by computer analysis of digitized images using Sigma Scan/Image software (Jandel Scientific). A dilution series of linear unit-length, cloned DNA was included on each gel as an internal standard for quantification.

Molecular Biological Techniques

All plasmids were purified from Escherichia coli by alkaline lysis and quantified using a fluorometer (TKO-100, Hoefer Scientific, San Francisco, Calif.). Restriction endonucleases were obtained from Promega Corp. (Madison, Wis.) or New England Biolabs, Inc. (Beverly, Mass.). Molecular biology techniques not described were performed according to standard methods known to the art (Maniatis et al., Molecular Cloning: A Laboratory Manual, 2 ed. Cold Spring Harbor Press, Cold Spring Harbor, N.Y., 1989). Data shown represent typical results from experiments that were repeated three or more times.

Results

Replication of DNA-B by Trans-expressed Rep Genes

Trans-expression vectors containing wild type rep genes were tested for the ability to replicate BGMV-GA DNA-B to determine if functional Rep protein was produced following inoculation of NT-1 suspension cells with rep trans-expression plasmids. Replication of DNA-B was detected in all treatments where DNA-B was co-inoculated with wild type DNA-A or rep trans-expression vectors containing wild type rep gene sequences, but not when DNA-B was co-inoculated with the non-replicating DNA-A or rep trans-expression vectors containing lethal rep mutations. Comparison of DNA-B replication levels between the various treatments showed that wild type DNA-A and pTrep23 replicated DNA-B to about equal levels, while DNA-B replication was reduced by ~99% in treatments inoculated with pTrep or pTrep23ΔE/C. These results show that all three types of trans-expression vectors were able to express functional wild type Rep protein, and that the ac3 gene increased the efficiency of rep dependent DNA-B replication as expected.

Trans-dominant Inhibition of BGMV-GA DNA-A Replication by Trans-expressed Rep Gene Mutants The ability of trans-expressed rep genes to interfere with geminiviral replication was tested by co-inoculating NT-1 suspension cells with trans-expression plasmids coding for wild type or mutant rep genes and wild type BGMV-GA DNA-A. Trans-expression vectors were inoculated in 10 to 100 fold mass excess (13 to 130 molar excess) relative to DNA-A as indicated. DNA-A replication was detected by Southern analysis with a probe derived from the cp gene of BGMV-GA. Supercoiled and open circular forms of dsDNA were detected in all treatments inoculated with wild type DNA-A after DpnI digestion to remove residual inoculum DNA. Digestion with NcoI, which cuts BGMV-GA DNA-A a single site at nucleotide 2,117, in addition to DpnI resulted in detection of linear, unit-length DNAs in all treatments inoculated with wild type DNA-A. Treatments inoculated with DNA-A plus pBS or DNA-A plus pTrep23P- (CaMV 35-S promoter deletion of pTrep23) were used as positive controls to establish DNA-A replication levels in the absence of trans-expressed geminiviral genes.

Inoculation efficiency was consistent within experiments but varied between experiments, probably due to differences in inoculation efficiency between the different batches of NT-1 suspension cells prepared for each experiment. For example, the level of DNA-A replication in positive control treatments typically varied less than 20% within experiments but ranged from averages of 0.05 to 0.5 ng/$\mu$g total DNA between experiments. Within experiments, no differences in DNA-A replication levels were detected between treatments where DNA-A was co-inoculated with either pBS or pTrep23P-. Also, no DNA-A replication products were detected in treatments where NT-1 suspension cells were inoculated with PGAADM, a BGMV-GA DNA-A clone which contains two replication abolishing mutations in the NTP-binding domain (E211R and K228H, Hanson et al., *Virology* 211:1–9, 1995). This treatment served as the negative control for DNA-A replication.

Replication of DNA-A was inhibited by pTrepX vectors containing function inhibiting mutations in the rep gene. DNA-nicking domain mutations Y103F and K106R and NTP-binding domain mutations K228H and D262R decreased BGMV-GA DNA-A replication by about 75 to 95%, respectively, relative to the positive control treatments when inoculated in 100 fold mass excess (130 fold molar excess). The ability of the pTrepX vectors to inhibit BGMV-GA DNA-A replication was diminished as the ratio of pTrepX to DNA-A was decreased in the inoculum. Little or no reduction in DNA-A accumulation was detected when pTrepX vectors were inoculated at 50 or 20 fold mass excess (65 or 26 fold molar excess) over DNA-A. Trans-expression vectors coding for wild type rep genes or rep genes containing a temperature sensitive mutation in the rep gene (E221R, Hanson et al., *Virology* 211:1–9, 1995) did not reduce BGMV-GA DNA-A accumulation even when inoculated in 100 fold excess over DNA-A (data not shown).

Effect of ac3 Gene Sequences on Trans-dominant Rep Genes

Since the ac3 gene functions to increase replication efficiency (Morris et al., *J. Gen. Virol.* 72:1205–1214, 1991; Pedersen and Hanley-Bowdoin, *Virology* 202:1070–1075, 1994), it was decided to test whether including sequences containing the ac3 gene in the rep trans-expression vectors would have an effect on trans-dominant activity of the rep gene mutants. Trans-expression vectors containing the ac3 gene in addition to the rep gene (pTrep23X vectors) were more efficient at inhibiting BGMV-GA DNA-A replication than the pTrepX vectors. When expressed with the ac3 gene, rep genes containing DNA-nicking or NTP-binding domain mutations reduced BGMV-GA DNA-A accumulation by 95–99% relative to the positive control treatment when inoculated in 50 fold excess. The rep gene mutants Y103F, K106R and D262R were slightly more efficient at inhibiting DNA-A replication than K228H. In contrast to the results with the pTrepX vectors, the pTrep23X vectors were able to efficiently interfere with DNA-A replication when inoculated at only 20 fold excess, the lowest ratio tested, reducing DNA-A accumulation by 95–99% relative to the positive control treatment. Similar to the results with the pTrepX vectors, rep genes containing the temperature sensitive mutation E221R (Hanson et al., *Virology* 211:1–9, 1995), alone or in combination with other mutations, did not interfere with DNA-A replication.

To determine if a functional ac3 gene was necessary for the observed enhancement of trans-dominant activity, the ability of pTrep23$\Delta$E/CX vectors to interfere with BGMV-GA DNA-A replication was tested. The pTrep23$\Delta$E/C vectors are identical to the pTrep23X vectors except that they contain an EcoRI (nt 1472) to ClaI (nt 1,299) deletion (FIG. 1) which removes codons 18 to 72 from the ac3 gene and abolishes the replication stimulating activity of the ac3 gene. Results from experiments where DNA-A was co-inoculated with pTrep23$\Delta$E/C vectors show that functional ac3 gene is not required for enhancement of rep-mediated trans-dominance. The DNA-nicking domain mutant Y103F and the NTP-binding domain mutant D262R were equally efficient at inhibiting BGMV-GA DNA-A replication when expressed from pTrep23X and ptrep$\Delta$E/CX vectors. These constructs reduced DNA-A accumulation to ~1% of the positive control treatment when inoculated in 50 fold excess over DNA-A. DNA-A replication was reduced by ~99% by Y103F and D262R mutants expressed from ptrep$\Delta$E/CX vectors at ratios of 25:1 and 10:1 over DNA-A.

Effect of Rep Gene Start Codon Mutations on Trans-dominance

Trans-dominance appeared to be mediated by the Rep protein since non-functional rep gene mutants inhibited DNA-A replication while the wild type rep gene did not, and because different rep gene mutants inhibited DNA-A replication to different degrees (Y103F=D262R>K228H), while rep genes containing the E221R mutation were not trans-dominant. Sequences overlapping the ac3 gene, which contain putative transcriptional termination signals, enhanced trans-dominance indicating that RNA-mediated mechanisms such as co-suppression (Dougherty and Parks, *Current Opinion in Cell Biology* 7:399–405, 1995) may contribute to trans-dominance. To test if an RNA-mediated mechanism was responsible for enhancement of rep-mediated trans-dominance, the start codon for the rep gene was mutated from ATG to ATC in pTrep23 to create pTrep23ATG- which was tested for the ability to inhibit replication of BGMV-GA DNA-A. No inhibition of DNA-A replication was observed when NT-1 suspension cells were co-inoculated with DNA-A and pTrep23ATG- indicating that an RNA-mediated mechanism was not responsible for enhanced trans-dominance. Therefore, nucleotides 1041–1492 increase the efficiency of trans-dominance by enhancing a Rep protein dependent mechanism. ps Inhibition of Heterologous Geminiviral Replication Since mutant rep genes from BGMV-GA were efficient trans-dominant inhibitors of BGMV-GA DNA-A replication, the ability of these same mutants to interfere with the replication of DNA-As from heterologous bean-infecting geminiviruses was tested. The DNA-nicking domain mutant Y103F and NTP-binding domain mutant D262R were tested for the ability to inhibit replication of DNA-As from BGMV-DR (Dominican Republic isolate of BGMV, Faria et al., *Phytopatology* 84:321–329, 1994), BGMV-BZ (Brazilian isolate of BGMV, Faria et al., *Phytopatology* 84:321–329, 1994), and bean dwarf mosaic virus (BDMV, Hidayat et al., *Phytopatology* 83:181–187, 1993). Infectious clones of DNA-A for each virus were co-inoculated with a 50 fold excess of the indicated rep trans-expression vector, and replication was detected by Southern analysis using a cp gene probe for each virus. Each DNA-A for these viruses replicated well and accumulated dsDNA replication products when inoculated with the promoterless rep trans-expression plasmid pTrep23P-. Replication of BGMV-DR DNA-A was inhibited by all four rep trans-expression vectors tested. In contrast to BGMV-DR, BGMV-BZ and BDMV DNA-A replication was not inhibited by pTrepY103F or pTrepD262R. However, replication of DNA-As from BGMV-BZ and BDMV was inhibited by both rep gene mutants when they were expressed with from the ptrepΔE/CX vector, indicating that BGMV-GA DNA-A nucleotide, 1,041–1,299 broaden the specificity of trans-dominant rep genes in addition to increasing their efficiency.

We claim:

1. A genetic construct comprising a plant promoter operably connected to a mutant geminiviral rep gene which is not natively associated with the promoter, the rep gene including a mutation in the NTP-binding or the DNA-nicking domain, the genetic construct also comprising a geminivirus ac3 gene, the genetic construct being effective, if introduced into and expressed in a transgenic plant cell, in inhibiting geminivirus DNA replication in that plant cell in a trans-dominant manner.

2. The genetic construct of claim 1, wherein the rep gene is a BGMV rep gene.

3. A genetic construction comprising a plant promoter and a mutant geminiviral rep gene which is not natively associated with the promoter operably connected to the promoter, the rep gene being from the BGMV-GA strain and including a mutation in the NTP-binding or the DNA-nicking domain of the rep gene, the genetic construction further comprising an ac3 gene from BGMV-GA (bases 1602–2033 SEQ ID NO: 7), the genetic construction being effective, if introduced into and expressed in a transgenic plant cell, in inhibiting geminivirus DNA replication in that plant cell in a trans-dominant manner.

4. A transgenic plant comprising in its genome the genetic construct of claim 1.

5. The transgenic plant of claim 4, wherein the rep gene is a BGMV rep gene.

6. The transgenic plant of claim 5, wherein the plant is a phaseoius plant.

7. A transgenic plant cell comprising in its genome the genetic construct of claim 1.

8. The plant cell of claim 7, wherein the genetic construct comprises a BGMV rep gene.

9. The plant cell of claim 8, wherein the cell is a phaseolus plant cell.

10. A seed of a transgenic plant comprising in its genome the genetic constructs of claim 1.

11. The plant seed of claim 10, wherein the genetic construct comprises a BGMV rep gene.

12. The plant seed of claim 11, wherein the seed is a phaseolus seed.

13. A method for making a plant cell resistant against infection by a geminivirus, comprising the steps of:

(a) making copies of a genetic construct including a plant promoter and a mutant geminiviral rep gene which is not natively associated with the promoter operably connected to the promoter, the rep gene including a mutation in the NTP-binding or the DNA-nicking domain of the rep gene, the genetic construct also including a geminivirus ac3 gene, the the genetic construction being effective, if introduced into and expressed in a transgenic plant cell, in inhibiting geminivirus DNA replication in that plant cell in a trans-dominant manner; and (b) introducing the genetic construct into the plant cell.

14. The method of claim 13, wherein the genetic construct comprises a BGMV rep gene.

15. The method of claim 13, wherein the plant is a phaseolus plant.

16. A genetic construction comprising 5' to 3' a promoter operative in plant cells;

a protein coding sequence operably connected to the promoter but which is not natively associated with the promoter, the coding sequence encoding a mutant form of a BGMV-GA geminivirus rep gene having a mutation in at least one of its NTP-binding domain and its DNA-nicking domain; and an ac3 gene from a BGMV-GA geminivirus;

the genetic construct effective when expressed in plant cells in expressing trans-dominant resistance to a geminivirus.

* * * * *

UNITED STATES PATENT AND TRADEMARK OFFICE
CERTIFICATE OF CORRECTION

Patent No.   : 6,118,048
Dated        : September 12, 2000
Inventor(s)  : Stephen F. Hanson and Douglas P. Maxwell It is certified that error appears in the above-identified patent and that said Letters Patent is hereby corrected as shown below:

The specification is amended to include, after the title, the following statement regarding federally sponsored research:

--This invention was made with United States government support awarded by the following agencies: USDA Award No: 95-8100-0296(CA); Hatch Nos: 3390, 3871, D390, N871. The United States has certain rights in this invention.--

Signed and Sealed this

Twenty-fourth Day of April, 2001

Attest:

NICHOLAS P. GODICI

Attesting Officer    Acting Director of the United States Patent and Trademark Office